(12) United States Patent
Connaris et al.

(10) Patent No.: US 10,953,078 B2
(45) Date of Patent: Mar. 23, 2021

(54) TREATMENT AND/OR PREVENTION OF SEPSIS

(71) Applicant: Pneumagen Limited, Fife (GB)

(72) Inventors: Helen Connaris, St. Andrews (GB); Garry Taylor, St. Andrews (GB); Hasan Yesilkaya, Leicester (GB); Peter Andrew, Leicester (GB)

(73) Assignee: Pneumagen Limited, Fife (GB)

( * ) Notice: Subject to any disclaimer, the term of this patent is extended or adjusted under 35 U.S.C. 154(b) by 0 days.

(21) Appl. No.: 16/332,920

(22) PCT Filed: Sep. 20, 2017

(86) PCT No.: PCT/GB2017/052800
§ 371 (c)(1),
(2) Date: Mar. 13, 2019

(87) PCT Pub. No.: WO2018/055365
PCT Pub. Date: Mar. 29, 2018

(65) Prior Publication Data
US 2019/0231853 A1 Aug. 1, 2019

(30) Foreign Application Priority Data
Sep. 20, 2016 (GB) .................................. 1616009

(51) Int. Cl.
| | | |
|---|---|---|
| A61K 38/47 | (2006.01) | |
| A61K 38/16 | (2006.01) | |
| A61P 31/04 | (2006.01) | |
| A61P 37/06 | (2006.01) | |
| C07K 16/12 | (2006.01) | |
| A61K 39/39 | (2006.01) | |
| C12N 9/24 | (2006.01) | |
| A61K 9/00 | (2006.01) | |
| A61K 39/00 | (2006.01) | |

(52) U.S. Cl.
CPC ............ *A61K 38/47* (2013.01); *A61K 9/0019* (2013.01); *A61K 9/0043* (2013.01); *A61K 38/164* (2013.01); *A61K 39/39* (2013.01); *A61P 31/04* (2018.01); *A61P 37/06* (2018.01); *C07K 16/1275* (2013.01); *C12N 9/2402* (2013.01); *A61K 2039/55544* (2013.01); *G01N 2333/315* (2013.01)

(58) Field of Classification Search
None
See application file for complete search history.

(56) References Cited

U.S. PATENT DOCUMENTS

| | | |
|---|---|---|
| 2002/0025320 A1 | 2/2002 | Boyaka et al. |
| 2004/0072256 A1 | 4/2004 | Mandelboim et al. |
| 2005/0084903 A1 | 4/2005 | Kim et al. |

FOREIGN PATENT DOCUMENTS

| | | |
|---|---|---|
| EP | 2799086 | 11/2014 |
| WO | 00/10398 | 3/2000 |
| WO | 2002/094869 | 11/2002 |
| WO | 2007/075921 | 7/2007 |
| WO | 2008/053486 | 5/2008 |
| WO | 2010/005737 | 1/2010 |
| WO | 2010/029312 | 3/2010 |
| WO | 2010/052492 | 5/2010 |
| WO | 2010/102112 | 9/2010 |
| WO | 2014/052621 | 4/2014 |
| WO | 2015/110831 | 7/2015 |
| WO | 2018/055370 | 3/2018 |
| WO | 2018/055373 | 3/2018 |

OTHER PUBLICATIONS

Baradaran et al. "Newcastie Disease Virus Hemagglutinin Neuraminidase as a Potential Cancer Targeting Agent", Journal of Cancer, 7,(4):462-466 (2016).
Chen et al. "Preserving Sialic Acid-dependent Pattern Recognition by CD24-Siglec G Interaction or Therapy of Polybacterial Sepsis" Nature Biotechnology, 29(5):428-435 (2011).
Connaris et al., "Enhancing the Receptor Affinity of the Sialic Acid-binding Domain of Vibrio cholerae Sialidase through Multivalency" Journal of Biological Chemistry, 284(11);7339-7351 (2009).
Connaris et al. "Prevention of influenza by targeting host receptors using engineered proteins" Proceedings of the National Academy of Sciences, 111(17):6401-6408 (2014).
Gasiorowski et al. "The impact of neuraminidase on apoptosis in cultures of blood lymphocytes isolated from rats bearing morris hepatoma" Cellular & molecular biology letters, pp. 389-399, URL: http://www.cmbl.org.pl/pdf/Vol9_p389.pdf (2004).
Govorkova et al. "Sialic Acid-Binding Protein Sp2CBMTD Protects Mice against Lethal Challenge with Emerging Influenza A (H7N9) Virus" Antimicrobial. Agents and Chemothe, American Society for Microbiology, 59(3):1495-1504 (2015).
Grata-Borkowska et al. "Effects of neuraminidase on apoptosis of blood lymphocytes in rats with implanted Morris tumor" Journal of physiology and pharmacology, an official journal of the Polish Physiological Society, p. 253, URL: http://www.jpp.krakow.pl/journal/archive/11_07_s5/pdf/253_11_07_s5_article.pdf (2007).
International Preliminary Report on Patentability corresponding to International Patent Application No. PCT/GB2017/052800, dated Mar. 26. 2019, 6 pages.
International Preliminary Report on Patentability corresponding to International Patent Application No. PCT/GB2017/052805, dated Mar. 26, 2019, 8 pages.
International Preliminary Report on Patentability corresponding to International Patent Application No. PCT/GB2017/052808, dated Mar. 26, 2019, 9 pages.

(Continued)

*Primary Examiner* — Rebecca E Prouty
(74) *Attorney, Agent, or Firm* — Myers Bigel, P.A.

(57) ABSTRACT

The disclosure provides molecules with an affinity for (or an ability to bind to), sialic acid, for use in compositions, medicaments and methods for the treatment of sepsis, its symptoms and sepsis associated pathologies and immune responses.

Figure 1:
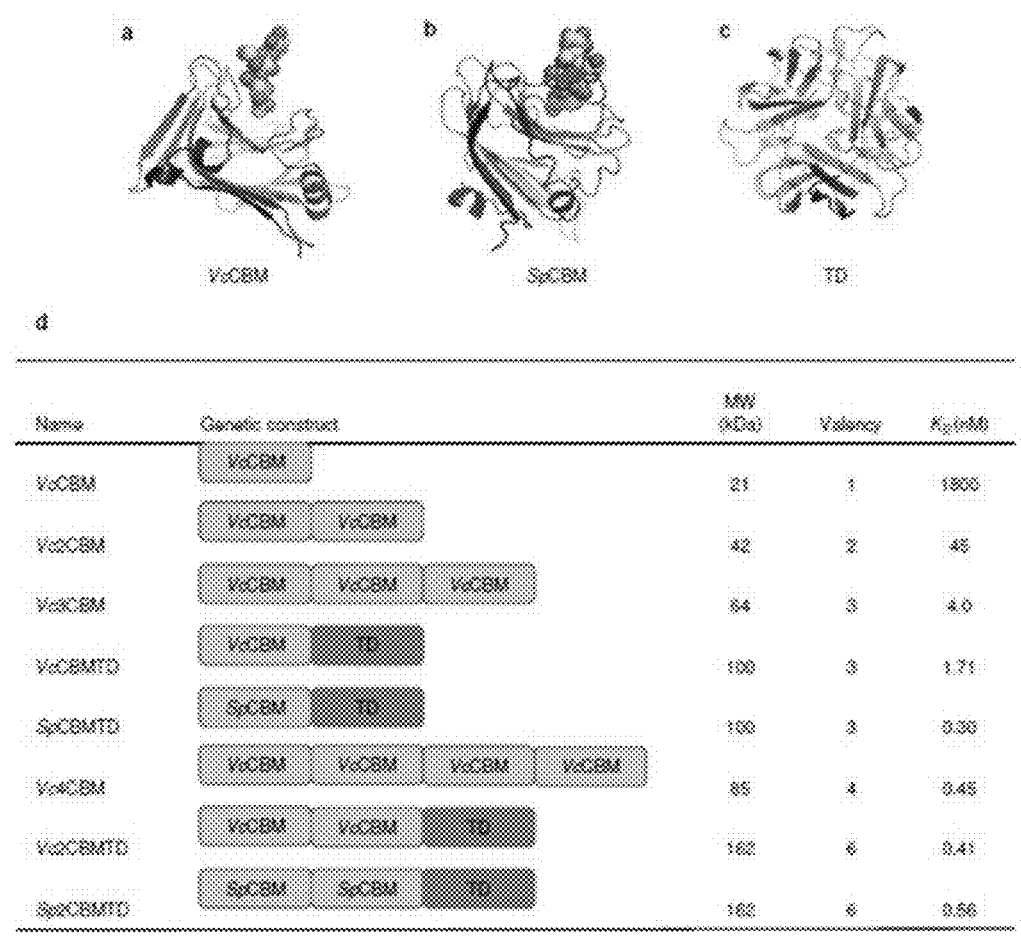

8 Claims, 8 Drawing Sheets
Specification includes a Sequence Listing.

(56) References Cited

OTHER PUBLICATIONS

Manco et al. "Pneumocoocal Neuraminidases A and B Both Have Essential Roles during Infection of the Respiratory Tract and Sepsis" Infection and Immunity, 74(7):4014-4020 (2006).

Simmons et al. "Immunospecific Regression of Methylcholanthrene Fibrosarcoma With the Use of Neuraminidase, II. Intratumor Injections of Neuraminidase" Sur, 71(4):556-564 (1972).

Simmons et al. "Regression of Established Methylcholanthrene Tumors by Intratumor Injections of Vibrio Cholerae Neuraminidase" Journal of Surgical Onco, 4(4):298-305 (1972) Abstract.

Written Opinion and International Search Report corresponding to International Patent Application No. PCT/GB2017/052800, dated Mar. 29, 2018, 10 pages.

Written Opinion and International Search Report corresponding to International Patent Application No. PCT/GB2017/052505, dated Mar. 29, 2018, 11 pages.

Written Opinion and International Search Report corresponding to International Patent Application No. PCT/GB2017/052808, dated Mar. 29, 2018, 16 pages.

Yang et al. "Structural characterization of the carbohydrate-binding module of NanA sialidase, a pneumococcal virulence factor" BMC Structural Biology, 15(1):15(2015).

Alias "Multivalent sialic acid binding proteins as novel therapeutics for influenza and parainfluenza infection" PhD Thesis at University of St Andrews, 252 pages (2013).

Knop "Stimulatory effect of Vibrio cholera neurammidas on the antibody response to various antigens" Immunology, 34:181-187(1978).

Research Councils UK, Gateway to Research "Exploiting a sialic acid binding domain" University of Andrews, 4 pages, accessed Jun. 1, 2017 from http://gtr.rcuk.ac.uk/projects?ref=BB%FE001912%2F1.

Rios et al. "Experimental Cancer Immunotherapy: modification of tumor cells to increase immunogenicity" Annals New York Academy of Sciences, 276:45-60 (1976).

Simmons et al. "Immunospecific Regression of methylcholanthrene Fibrosarcoma With the Use of Neuraminidase: III. Synergistic Effect of BCG and Neuraminidase Treated Tumor Cells" Ann. Surg. 176(2):188-194 (1972).

SEQUENCE LISTING

```
<160> NUMBER OF SEQ ID NOS: 10

<210> SEQ ID NO 1
<211> LENGTH: 781
<212> TYPE: PRT
<213> ORGANISM: Vibrio cholerae

<400> SEQUENCE: 1

Met Arg Phe Lys Asn Val Lys Lys Thr Ala Leu Met Leu Ala Met Phe
1               5                   10                  15

Gly Met Ala Thr Ser Ser Asn Ala Ala Leu Phe Asp Tyr Asn Ala Thr
                20                  25                  30

Gly Asp Thr Glu Phe Asp Ser Pro Ala Lys Gln Gly Trp Met Gln Asp
            35                  40                  45

Asn Thr Asn Asn Gly Ser Gly Val Leu Thr Asn Ala Asp Gly Met Pro
        50                  55                  60

Ala Trp Leu Val Gln Gly Ile Gly Gly Arg Ala Gln Trp Thr Tyr Ser
65                  70                  75                  80

Leu Ser Thr Asn Gln His Ala Gln Ala Ser Ser Phe Gly Trp Arg Met
                85                  90                  95

Thr Thr Glu Met Lys Val Leu Ser Gly Gly Met Ile Thr Asn Tyr Tyr
                100                 105                 110
```

```
Ala Asn Gly Thr Gln Arg Val Leu Pro Ile Ile Ser Leu Asp Ser Ser
            115                 120                 125
Gly Asn Leu Val Val Glu Phe Glu Gly Gln Thr Gly Arg Thr Val Leu
130                 135                 140
Ala Thr Gly Thr Ala Ala Thr Glu Tyr His Lys Phe Glu Leu Val Phe
145                 150                 155                 160
Leu Pro Gly Ser Asn Pro Ser Ala Ser Phe Tyr Phe Asp Gly Lys Leu
                165                 170                 175
Ile Arg Asp Asn Ile Gln Pro Thr Ala Ser Lys Gln Asn Met Ile Val
            180                 185                 190
Trp Gly Asn Gly Ser Ser Asn Thr Asp Gly Val Ala Ala Tyr Arg Asp
        195                 200                 205
Ile Lys Phe Glu Ile Gln Gly Asp Val Ile Phe Arg Gly Pro Asp Arg
        210                 215                 220
Ile Pro Ser Ile Val Ala Ser Ser Val Thr Pro Gly Val Val Thr Ala
225                 230                 235                 240
Phe Ala Glu Lys Arg Val Gly Gly Asp Pro Gly Ala Leu Ser Asn
                245                 250                 255
Thr Asn Asp Ile Ile Thr Arg Thr Ser Arg Asp Gly Gly Ile Thr Trp
            260                 265                 270
Asp Thr Glu Leu Asn Leu Thr Glu Gln Ile Asn Val Ser Asp Glu Phe
        275                 280                 285
Asp Phe Ser Asp Pro Arg Pro Ile Tyr Asp Pro Ser Ser Asn Thr Val
        290                 295                 300
Leu Val Ser Tyr Ala Arg Trp Pro Thr Asp Ala Ala Gln Asn Gly Asp
305                 310                 315                 320
Arg Ile Lys Pro Trp Met Pro Asn Gly Ile Phe Tyr Ser Val Tyr Asp
                325                 330                 335
Val Ala Ser Gly Asn Trp Gln Ala Pro Ile Asp Val Thr Asp Gln Val
            340                 345                 350
Lys Glu Arg Ser Phe Gln Ile Ala Gly Trp Gly Gly Ser Glu Leu Tyr
        355                 360                 365
Arg Arg Asn Thr Ser Leu Asn Ser Gln Gln Asp Trp Gln Ser Asn Ala
        370                 375                 380
Lys Ile Arg Ile Val Asp Gly Ala Ala Asn Gln Ile Gln Val Ala Asp
385                 390                 395                 400
Gly Ser Arg Lys Tyr Val Val Thr Leu Ser Ile Asp Glu Ser Gly Gly
                405                 410                 415
Leu Val Ala Asn Leu Asn Gly Val Ser Ala Pro Ile Ile Leu Gln Ser
            420                 425                 430
Glu His Ala Lys Val His Ser Phe His Asp Tyr Glu Leu Gln Tyr Ser
        435                 440                 445
Ala Leu Asn His Thr Thr Thr Leu Phe Val Asp Gly Gln Gln Ile Thr
        450                 455                 460
Thr Trp Ala Gly Glu Val Ser Gln Glu Asn Asn Ile Gln Phe Gly Asn
465                 470                 475                 480
Ala Asp Ala Gln Ile Asp Gly Arg Leu His Val Gln Lys Ile Val Leu
                485                 490                 495
Thr Gln Gln Gly His Asn Leu Val Glu Phe Asp Ala Phe Tyr Leu Ala
            500                 505                 510
Gln Gln Thr Pro Glu Val Glu Lys Asp Leu Glu Lys Leu Gly Trp Thr
        515                 520                 525
Lys Ile Lys Thr Gly Asn Thr Met Ser Leu Tyr Gly Asn Ala Ser Val
```

```
                530                 535                 540
Asn Pro Gly Pro Gly His Gly Ile Thr Leu Thr Arg Gln Gln Asn Ile
545                 550                 555                 560

Ser Gly Ser Gln Asn Gly Arg Leu Ile Tyr Pro Ala Ile Val Leu Asp
                565                 570                 575

Arg Phe Phe Leu Asn Val Met Ser Ile Tyr Ser Asp Asp Gly Gly Ser
                580                 585                 590

Asn Trp Gln Thr Gly Ser Thr Leu Pro Ile Pro Phe Arg Trp Lys Ser
                595                 600                 605

Ser Ser Ile Leu Glu Thr Leu Glu Pro Ser Glu Ala Asp Met Val Glu
                610                 615                 620

Leu Gln Asn Gly Asp Leu Leu Leu Thr Ala Arg Leu Asp Phe Asn Gln
625                 630                 635                 640

Ile Val Asn Gly Val Asn Tyr Ser Pro Arg Gln Gln Phe Leu Ser Lys
                645                 650                 655

Asp Gly Gly Ile Thr Trp Ser Leu Leu Glu Ala Asn Asn Ala Asn Val
                660                 665                 670

Phe Ser Asn Ile Ser Thr Gly Thr Val Asp Ala Ser Ile Thr Arg Phe
                675                 680                 685

Glu Gln Ser Asp Gly Ser His Phe Leu Leu Phe Thr Asn Pro Gln Gly
                690                 695                 700

Asn Pro Ala Gly Thr Asn Gly Arg Gln Asn Leu Gly Leu Trp Phe Ser
705                 710                 715                 720

Phe Asp Glu Gly Val Thr Trp Lys Gly Pro Ile Gln Leu Val Asn Gly
                725                 730                 735

Ala Ser Ala Tyr Ser Asp Ile Tyr Gln Leu Asp Ser Glu Asn Ala Ile
                740                 745                 750

Val Ile Val Glu Thr Asp Asn Ser Asn Met Arg Ile Leu Arg Met Pro
                755                 760                 765

Ile Thr Leu Leu Lys Gln Lys Leu Thr Leu Ser Gln Asn
                770                 775                 780

<210> SEQ ID NO 2
<211> LENGTH: 1035
<212> TYPE: PRT
<213> ORGANISM: Streptococcus pneumoniae

<400> SEQUENCE: 2

Met Ser Tyr Phe Arg Asn Arg Asp Ile Asp Ile Glu Arg Asn Ser Met
1               5                   10                  15

Asn Arg Ser Val Gln Glu Arg Lys Cys Arg Tyr Ser Ile Arg Lys Leu
                20                  25                  30

Ser Val Gly Ala Val Ser Met Ile Val Gly Ala Val Val Phe Gly Thr
            35                  40                  45

Ser Pro Val Leu Ala Gln Glu Gly Ala Ser Glu Gln Pro Leu Ala Asn
        50                  55                  60

Glu Thr Gln Leu Ser Gly Glu Ser Ser Thr Leu Thr Asp Thr Glu Lys
65                  70                  75                  80

Ser Gln Pro Ser Ser Glu Thr Glu Leu Ser Gly Asn Lys Gln Glu Gln
                85                  90                  95

Glu Arg Lys Asp Lys Gln Glu Glu Lys Ile Pro Arg Asp Tyr Tyr Ala
                100                 105                 110

Arg Asp Leu Glu Asn Val Glu Thr Val Ile Glu Lys Glu Asp Val Glu
            115                 120                 125
```

-continued

```
Thr Asn Ala Ser Asn Gly Gln Arg Val Asp Leu Ser Ser Glu Leu Asp
        130                 135                 140

Lys Leu Lys Lys Leu Glu Asn Ala Thr Val His Met Glu Phe Lys Pro
145                 150                 155                 160

Asp Ala Lys Ala Pro Ala Phe Tyr Asn Leu Phe Ser Val Ser Ser Ala
                165                 170                 175

Thr Lys Lys Asp Glu Tyr Phe Thr Met Ala Val Tyr Asn Asn Thr Ala
            180                 185                 190

Thr Leu Glu Gly Arg Gly Ser Asp Gly Lys Gln Phe Tyr Asn Asn Tyr
        195                 200                 205

Asn Asp Ala Pro Leu Lys Val Lys Pro Gly Gln Trp Asn Ser Val Thr
210                 215                 220

Phe Thr Val Glu Lys Pro Thr Ala Glu Leu Pro Lys Gly Arg Val Arg
225                 230                 235                 240

Leu Tyr Val Asn Gly Val Leu Ser Arg Thr Ser Leu Arg Ser Gly Asn
                245                 250                 255

Phe Ile Lys Asp Met Pro Asp Val Thr His Val Gln Ile Gly Ala Thr
            260                 265                 270

Lys Arg Ala Asn Asn Thr Val Trp Gly Ser Asn Leu Gln Ile Arg Asn
        275                 280                 285

Leu Thr Val Tyr Asn Arg Ala Leu Thr Pro Glu Glu Val Gln Lys Arg
290                 295                 300

Ser Gln Leu Phe Lys Arg Ser Asp Leu Glu Lys Leu Pro Glu Gly
305                 310                 315                 320

Ala Ala Leu Thr Glu Lys Thr Asp Ile Phe Glu Ser Gly Arg Asn Gly
                325                 330                 335

Lys Pro Asn Lys Asp Gly Ile Lys Ser Tyr Arg Ile Pro Ala Leu Leu
            340                 345                 350

Lys Thr Asp Lys Gly Thr Leu Ile Ala Gly Ala Asp Glu Arg Arg Leu
        355                 360                 365

His Ser Ser Asp Trp Gly Asp Ile Gly Met Val Ile Arg Arg Ser Glu
370                 375                 380

Asp Asn Gly Lys Thr Trp Gly Asp Arg Val Thr Ile Thr Asn Leu Arg
385                 390                 395                 400

Asp Asn Pro Lys Ala Ser Asp Pro Ser Ile Gly Ser Pro Val Asn Ile
                405                 410                 415

Asp Met Val Leu Val Gln Asp Pro Glu Thr Lys Arg Ile Phe Ser Ile
            420                 425                 430

Tyr Asp Met Phe Pro Glu Gly Lys Gly Ile Phe Gly Met Ser Ser Gln
        435                 440                 445

Lys Glu Glu Ala Tyr Lys Lys Ile Asp Gly Lys Thr Tyr Gln Ile Leu
450                 455                 460

Tyr Arg Glu Gly Glu Lys Gly Ala Tyr Thr Ile Arg Glu Asn Gly Thr
465                 470                 475                 480

Val Tyr Thr Pro Asp Gly Lys Ala Thr Asp Tyr Arg Val Val Val Asp
                485                 490                 495

Pro Val Lys Pro Ala Tyr Ser Asp Lys Gly Asp Leu Tyr Lys Gly Asn
            500                 505                 510

Gln Leu Leu Gly Asn Ile Tyr Phe Thr Thr Asn Lys Thr Ser Pro Phe
        515                 520                 525

Arg Ile Ala Lys Asp Ser Tyr Leu Trp Met Ser Tyr Ser Asp Asp Asp
530                 535                 540

Gly Lys Thr Trp Ser Ala Pro Gln Asp Ile Thr Pro Met Val Lys Ala
```

-continued

```
        545                 550                 555                 560
Asp Trp Met Lys Phe Leu Gly Val Gly Pro Gly Thr Gly Ile Val Leu
                565                 570                 575
Arg Asn Gly Pro His Lys Gly Arg Ile Leu Ile Pro Val Tyr Thr Thr
                580                 585                 590
Asn Asn Val Ser His Leu Asn Gly Ser Gln Ser Ser Arg Ile Ile Tyr
                595                 600                 605
Ser Asp Asp His Gly Lys Thr Trp His Ala Gly Glu Ala Val Asn Asp
    610                 615                 620
Asn Arg Gln Val Asp Gly Gln Lys Ile His Ser Ser Thr Met Asn Asn
625                 630                 635                 640
Arg Arg Ala Gln Asn Thr Glu Ser Thr Val Val Gln Leu Asn Asn Gly
                645                 650                 655
Asp Val Lys Leu Phe Met Arg Gly Leu Thr Gly Asp Leu Gln Val Ala
                660                 665                 670
Thr Ser Lys Asp Gly Gly Val Thr Trp Glu Lys Asp Ile Lys Arg Tyr
                675                 680                 685
Pro Gln Val Lys Asp Val Tyr Val Gln Met Ser Ala Ile His Thr Met
                690                 695                 700
His Glu Gly Lys Glu Tyr Ile Ile Leu Ser Asn Ala Gly Gly Pro Lys
705                 710                 715                 720
Arg Glu Asn Gly Met Val His Leu Ala Arg Val Glu Glu Asn Gly Glu
                725                 730                 735
Leu Thr Trp Leu Lys His Asn Pro Ile Gln Lys Gly Glu Phe Ala Tyr
                740                 745                 750
Asn Ser Leu Gln Glu Leu Gly Asn Gly Glu Tyr Gly Ile Leu Tyr Glu
                755                 760                 765
His Thr Glu Lys Gly Gln Asn Ala Tyr Thr Leu Ser Phe Arg Lys Phe
                770                 775                 780
Asn Trp Asp Phe Leu Ser Lys Asp Leu Ile Ser Pro Thr Glu Ala Lys
785                 790                 795                 800
Val Lys Arg Thr Arg Glu Met Gly Lys Gly Val Ile Gly Leu Glu Phe
                805                 810                 815
Asp Ser Glu Val Leu Val Asn Lys Ala Pro Thr Leu Gln Leu Ala Asn
                820                 825                 830
Gly Lys Thr Ala Arg Phe Met Thr Gln Tyr Asp Thr Lys Thr Leu Leu
                835                 840                 845
Phe Thr Val Asp Ser Glu Asp Met Gly Gln Lys Val Thr Gly Leu Ala
    850                 855                 860
Glu Gly Ala Ile Glu Ser Met His Asn Leu Pro Val Ser Val Ala Gly
865                 870                 875                 880
Thr Lys Leu Ser Asn Gly Met Asn Gly Ser Glu Ala Ala Val His Glu
                885                 890                 895
Val Pro Glu Tyr Thr Gly Pro Leu Gly Thr Ser Gly Glu Glu Pro Ala
                900                 905                 910
Pro Thr Val Glu Lys Pro Glu Tyr Thr Gly Pro Leu Gly Thr Ser Gly
                915                 920                 925
Glu Glu Pro Ala Pro Thr Val Glu Lys Pro Glu Tyr Thr Gly Pro Leu
    930                 935                 940
Gly Thr Ala Gly Glu Glu Ala Ala Pro Thr Val Glu Lys Pro Glu Phe
945                 950                 955                 960
Thr Gly Gly Val Asn Gly Thr Glu Pro Ala Val His Glu Ile Ala Glu
                965                 970                 975
```

Tyr Lys Gly Ser Asp Ser Leu Val Thr Leu Thr Thr Lys Glu Asp Tyr
            980                 985                 990

Thr Tyr Lys Ala Pro Leu Ala Gln Gln Ala Leu Pro Glu Thr Gly Asn
        995                 1000                1005

Lys Glu Ser Asp Leu Leu Ala Ser Leu Gly Leu Thr Ala Phe Phe
    1010                1015                1020

Leu Gly Leu Phe Thr Leu Gly Lys Lys Arg Glu Gln
    1025                1030                1035

<210> SEQ ID NO 3
<211> LENGTH: 185
<212> TYPE: PRT
<213> ORGANISM: Streptococcus pneumoniae

<400> SEQUENCE: 3

Val Ile Glu Lys Glu Asp Val Glu Thr Asn Ala Ser Asn Gly Gln Arg
1               5                   10                  15

Val Asp Leu Ser Ser Glu Leu Asp Lys Leu Lys Lys Leu Glu Asn Ala
            20                  25                  30

Thr Val His Met Glu Phe Lys Pro Asp Ala Lys Ala Pro Ala Phe Tyr
        35                  40                  45

Asn Leu Phe Ser Val Ser Ser Ala Thr Lys Lys Asp Glu Tyr Phe Thr
    50                  55                  60

Met Ala Val Tyr Asn Asn Thr Ala Thr Leu Glu Gly Arg Gly Ser Asp
65                  70                  75                  80

Gly Lys Gln Phe Tyr Asn Asn Tyr Asn Asp Ala Pro Leu Lys Val Lys
                85                  90                  95

Pro Gly Gln Trp Asn Ser Val Thr Phe Thr Val Glu Lys Pro Thr Ala
            100                 105                 110

Glu Leu Pro Lys Gly Arg Val Arg Leu Tyr Val Asn Gly Val Leu Ser
        115                 120                 125

Arg Thr Ser Leu Arg Ser Gly Asn Phe Ile Lys Asp Met Pro Asp Val
    130                 135                 140

Thr His Val Gln Ile Gly Ala Thr Lys Arg Ala Asn Asn Thr Val Trp
145                 150                 155                 160

Gly Ser Asn Leu Gln Ile Arg Asn Leu Thr Val Tyr Asn Arg Ala Leu
                165                 170                 175

Thr Pro Glu Glu Val Gln Lys Arg Ser
            180                 185

<210> SEQ ID NO 4
<211> LENGTH: 5
<212> TYPE: PRT
<213> ORGANISM: Artificial Sequence
<220> FEATURE:
<223> OTHER INFORMATION: Linker

<400> SEQUENCE: 4

Ala Leu Asn Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Linker

<400> SEQUENCE: 5

```
Leu Gln Ala Leu Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Linker

<400> SEQUENCE: 6

Gly Gly Asn Ser Gly
1               5

<210> SEQ ID NO 7
<211> LENGTH: 10
<212> TYPE: PRT
<213> ORGANISM: Artificial Sequence
<220> FEATURE:
<223> OTHER INFORMATION: Linker

<400> SEQUENCE: 7

Ala Leu Asn Gly Ser Gly Gly Gly Ser Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Linker

<400> SEQUENCE: 8

Leu Gln Ala Leu Gly Gly Gly Gly Ser Leu
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Linker

<400> SEQUENCE: 9

Ala Leu Asn Gly Ser Gly Gly Gly Ser Gly Gly Gly Ser Gly
1               5                   10                  15

<210> SEQ ID NO 10
<211> LENGTH: 438
<212> TYPE: PRT
<213> ORGANISM: Pseudomonas aeruginosa

<400> SEQUENCE: 10

Met Asn Thr Tyr Phe Asp Ile Pro His Arg Leu Val Gly Lys Ala Leu
1               5                   10                  15

Tyr Glu Ser Tyr Tyr Asp His Phe Gly Gln Met Asp Ile Leu Ser Asp
                20                  25                  30

Gly Ser Leu Tyr Leu Ile Tyr Arg Arg Ala Thr Glu His Val Gly Gly
            35                  40                  45

Ser Asp Gly Arg Val Val Phe Ser Lys Leu Glu Gly Ile Trp Ser
        50                  55                  60

Ala Pro Thr Ile Val Ala Gln Ala Gly Gly Gln Asp Phe Arg Asp Val
65                  70                  75                  80
```

```
Ala Gly Gly Thr Met Pro Ser Gly Arg Ile Val Ala Ala Ser Thr Val
                 85                  90                  95

Tyr Glu Thr Gly Glu Val Lys Val Tyr Val Ser Asp Asp Ser Gly Val
            100                 105                 110

Thr Trp Val His Lys Phe Thr Leu Ala Arg Gly Gly Ala Asp Tyr Asn
            115                 120                 125

Phe Ala His Gly Lys Ser Phe Gln Val Gly Ala Arg Tyr Val Ile Pro
130                 135                 140

Leu Tyr Ala Ala Thr Gly Val Asn Tyr Glu Leu Lys Trp Leu Glu Ser
145                 150                 155                 160

Ser Asp Gly Gly Glu Thr Trp Gly Glu Gly Ser Thr Ile Tyr Ser Gly
                165                 170                 175

Asn Thr Pro Tyr Asn Glu Thr Ser Tyr Leu Pro Val Gly Asp Gly Val
                180                 185                 190

Ile Leu Ala Val Ala Arg Val Gly Ser Gly Ala Gly Ala Leu Arg
                195                 200                 205

Gln Phe Ile Ser Leu Asp Asp Gly Gly Thr Trp Thr Asp Gln Gly Asn
210                 215                 220

Val Thr Ala Gln Asn Gly Asp Ser Thr Asp Ile Leu Val Ala Pro Ser
225                 230                 235                 240

Leu Ser Tyr Ile Tyr Ser Glu Gly Gly Thr Pro His Val Val Leu Leu
                245                 250                 255

Tyr Thr Asn Arg Thr Thr His Phe Cys Tyr Tyr Arg Thr Ile Leu Leu
                260                 265                 270

Ala Lys Ala Val Ala Gly Ser Ser Gly Trp Thr Glu Arg Val Pro Val
275                 280                 285

Tyr Ser Ala Pro Ala Ala Ser Gly Tyr Thr Ser Gln Val Val Leu Gly
                290                 295                 300

Gly Arg Arg Ile Leu Gly Asn Leu Phe Arg Glu Thr Ser Ser Thr Thr
305                 310                 315                 320

Ser Gly Ala Tyr Gln Phe Glu Val Tyr Leu Gly Gly Val Pro Asp Phe
                325                 330                 335

Glu Ser Asp Trp Phe Ser Val Ser Asn Ser Leu Tyr Thr Leu Ser
                340                 345                 350

His Gly Leu Gln Arg Ser Pro Arg Arg Val Val Val Glu Phe Ala Arg
                355                 360                 365

Ser Ser Ser Pro Ser Thr Trp Asn Ile Val Met Pro Ser Tyr Phe Asn
                370                 375                 380

Asp Gly Gly His Lys Gly Ser Gly Ala Gln Val Glu Val Gly Ser Leu
385                 390                 395                 400

Asn Ile Arg Leu Gly Thr Gly Ala Ala Val Trp Gly Thr Gly Tyr Phe
                405                 410                 415

Gly Gly Ile Asp Asn Ser Ala Thr Thr Arg Phe Ala Thr Gly Tyr Tyr
                420                 425                 430

Arg Val Arg Ala Trp Ile
                435
```

TREATMENT AND/OR PREVENTION OF SEPSIS

STATEMENT OF PRIORITY

This application is a 35 U.S.C. § 371 national phase application of International Application Serial No. PCT/GB2017/052800, filed Sep. 20, 2017, which claims the benefit, of United Kingdom Patent Application No. 1616009.5, filed Sep. 20, 2016, the entire contents of each of which are incorporated by reference herein.

FIELD OF THE INVENTION

The invention provides molecules for use in compositions, medicaments and methods for the treatment of sepsis, its symptoms and sepsis associated pathologies and immune responses.

BACKGROUND OF THE INVENTION

Sepsis is a life-threatening condition that is most commonly caused by bacteria in the bloodstream, a condition known as bacteraemia. Pathogenic bacteria originating from a primary infection location, such as the lungs or urinary tract, release toxins that can provoke a dysregulation of the innate immune response, leading to host tissue and organ damage[1].

Bacterial sepsis is a worldwide problem, generally resulting from nosocomial polybacterial infections, and is responsible for 25% intensive care admissions with a survival rate of around 50%[2].

While conventional antibiotics may be effective in killing pathogenic microorganisms in sepsis patients, they can also accelerate the release of pro-inflammatory components causing severe sepsis and shock. Alternative compounds of interest for sepsis therapy include natural occurring antimicrobial peptides (AMPs), which target pathogenic bacteria and fungi by displaying different defense mechanisms such as membrane disruption, with some having immunomodulatory activities[4]. AMPs mainly function by disabling/killing pathogen without releasing pro-inflammatory agents. However, there are several challenges with the use of AMPs as therapeutics due to their limited pharmaceutical application such as high toxicity in most tissues, as well as the likelihood of microbial resistances. Attempts to design synthetic based AMPs to reduce toxicity and stability issues are in developments.

Multivalent Family 40 CBMs (mCBM40s) target and bind to host cell surface sialic acid receptors with high affinity[7,8]. These engineered mCBM40s also display immunomodulatory activities when given intranasally either alone, or in respiratory pathogen-challenged mouse models[5,9].

Despite the use of antibiotics as a control strategy for bacterial sepsis, the rise in antibiotic resistance by bloodstream bacterial isolates in recent years has highlighted an urgent need for novel compounds, therapies and regimes for the treatment and management of sepsis, its symptoms and pathologies[3].

SUMMARY OF THE INVENTION

The present disclosure is based on the finding that molecules with affinity for (or an ability to bind to) sialic acid and in particular sialylated cell surfaces (these including cell surface sialic acid receptors), find utility in the treatment and/or prevention of sepsis.

As such, the present disclosure provides a sialic acid binding molecule for use in the treatment and/or prevention of sepsis and/or one or more symptoms thereof. Further provided is the use of a sialic acid binding molecule in the manufacture of a medicament for use in the treatment and/or prevention of sepsis and/or one or more symptoms thereof.

It should be understood that throughout this specification, the terms "comprise", "comprising" and/or "comprises" is/are used to denote aspects and embodiments of this invention that "comprise" a particular feature or features. It should be understood that this/these terms may also encompass aspects and/or embodiments which "consist essentially of" or "consist of" the relevant feature or features.

The disclosure also relates to a method of treating or preventing sepsis and/or one or more symptoms thereof, said method comprising the steps of administering to a subject in need thereof, a therapeutically effective amount of a sialic acid binding molecule.

The term "sepsis" is applied to a number of diseases, conditions and/or syndromes which may have an infectious (for example viral, bacterial and/or fungal) aetiology. For example, term "sepsis", may embrace those disease states, conditions or syndromes referred to as SIRS (systemic inflammatory response syndrome: indicated by the presence of two or more of abnormal body temperature, heart rate, respiratory rate or blood gas and white blood cell count), sepsis (which is often defined as "SIRS in response to an infectious process"), severe sepsis (that is sepsis with sepsis-induced organ dysfunction or tissue hypoperfusion (which itself might manifest as hypotension, elevated lactate or decreased urine output) and septic shock (severe sepsis plus persistently low blood pressure despite, for example, the administration of intravenous fluids).

The term "sepsis" is most often applied to diseases, conditions and/or syndromes which result from "bacterial sepsis". Bacterial sepsis may stem from the presence of bacteria in blood and may sometimes be referred to as "bacteraemia" or "septicemia". The term "sepsis" may also embrace diseases and/or conditions which are caused or contributed to by the presence of bacterial components such as LPS, toxins and/or membrane fragments in the blood. Components of this type may originate from primary infections present in other tissues and/or organs, for example, infections present in the lungs, brain, skin, urinary tract, pelvis and/or abdomen.

Sepsis can be a very severe condition which occasionally leads to multiple organ failure and death. There may be a number of pathologies and/or symptoms associated with each type of sepsis and these will be collectively referred to hereinafter as "sepsis associated pathologies". For example, sepsis associated pathologies may include, for example, fever, increased heart rate, increased rate of respiration and/or low blood pressure.

The primary mechanism which underpins the pathology of sepsis and many of the symptoms and outcomes associated therewith is an exacerbated, exaggerated and/or inappropriate host immune response. This exacerbated immune response (which is the body's response to infection) leads to host tissue damage and/or organ damage/failure.

The exacerbated or inappropriate immune response may include the dysregulation of innate immune responses as well as the production and/or over production of certain pro-coagulation cytokines (including, for example, tumour necrosis factor, interleukin 1 and interleukin 6).

The term "subject" or "subject in need thereof" as used herein, may embrace any subject who has or is at risk of developing "sepsis". For example, the subject may be one who is predisposed or susceptible to sepsis. The "subject" may be one who has been diagnosed as suffering from one or more of the "sepsis" type pathologies described herein. The "subject" may be one who has an infection and who may go on to develop sepsis.

It should be understood that the various "sepsis" associated pathologies described above include conditions, syndromes and/or effects that may otherwise be described as "symptoms" of sepsis. As such, one or more of the sialic acid binding molecules described herein may be for use in the treatment and/or prevention of any (one or more) of these symptoms. For example, this disclosure provides any one or more of the sialic acid binding molecules described herein, for use in the treatment and/or prevention of sepsis associated:fever; immune response(s); low blood pressure; increased heart rate and/or increased rate of respiration.

Further, any of the sialic acid binding molecules described herein may be used in the manufacture of medicaments and methods for treating or preventing the same.

Without wishing to be bound by theory, it is suggested that the sialic acid binding molecules described herein are effective to dampen, suppress or inhibit the pro-inflammatory cytokine cascade that is a pre-cursor to sepsis or one or more of the symptom(s) thereof. Nevertheless, it is also suggested that the sialic acid binding molecules described herein (including the CBM-type molecules) can be used to prevent the invasive disease and/or infection(s) that can lead to sepsis. Further the sialic acid binding molecules may help reduce the pathogen burden within a subject (and thus reduce the risk of sepsis) by reducing overall pathogen carriage and/or colonization. Again, without wishing to be bound by theory, these effects may be associated with, or linked to, the sialic acid binding nature of the molecules described herein; by binding to sialic acid, the sialic acid binding molecule (for example the CBM) prevents a pathogen from exploiting (i.e. binding to or interacting with) the presence of sialic acid in certain host receptors.

As stated, the sialic acid binding molecules which are to be used in the treatment and/or prevention of sepsis or a symptom (or pathology) thereof, exhibit an ability to bind to sialic acid of the type that is commonly found on or in cell membranes and/or cell surface receptors.

Useful sialic acid binding molecules may take any form and/or belong to any class of molecule or compound (for example they may be proteins, peptides, carbohydrates, antibodies and the like) and term "sialic acid" embraces all forms of N- or O-substituted neuraminic acid and includes all synthetic, naturally occurring and/or modified forms thereof. Sialic acids may be found as components of cell surface molecules, glycoproteins and glycolipids. Most often, sialic acids are present at the end (terminal regions) of sugar chains connected to cell membranes and/or proteins. For example, some cells of the human upper respiratory tract comprise α-2,6-linked sialic acid receptors and other cells of the upper and lower respiratory tracts comprise α-2,3-linked sialic acid receptors. The sialic acid family encompasses a number (approximately 50) of derivatives that may result from acetylation, glycolylation, lactonisation and methylation at C4, C5, C7, C8 and C9. All such derivatives are to be embraced by the term "sialic acid".

Furthermore, sialic acids are found linked α(2,3) or α(2,6) to Gal and GalNAc or α(2,8) or α(2,9) to another sialic acid. Accordingly, it is important to understand that while the term "sialic acid" is used throughout this specification, it encompasses all derivatives, analogues or variants (either naturally occurring or synthetically generated) thereof as well as monomers, dimers, trimers, oligomers, polymers or concatamers comprising the same.

Thus, a sialic acid binding molecule of this disclosure (and for use as described herein) comprises a moiety which exhibits an affinity for sialic acid—including all forms of sialic acid described above and any form of sialic acid present on the surface of a cell (perhaps as part of a cell surface receptor), for example a mammalian cell. These various forms of sialic acid may be collectively referred to as "sialic acid moieties".

The sialic acid binding molecules of this disclosure exhibit an affinity for sialic acid and as such they may bind/couple to and/or associate with one or more sialic acid moieties. Thus, the term "sialic acid binding molecule" may further encompass any fragment of a whole sialic acid binding molecule which retains an ability to bind to or otherwise couple or associate with a sialic acid moiety.

Sialic acid binding molecules for use may comprise a single sialic acid binding molecule (a monomeric or monovalent molecule, for example) or, alternatively, two or more sialic acid binding molecules—which two or more molecules may be the same or different—a polymeric or multivalent molecule, for example.

A sialic acid binding molecule for use may comprise, consist essentially of or consist of, one or more of the sialic acid binding molecules known as "carbohydrate binding modules" (CBMs). CBMs suitable for use exhibit an affinity for sialic acid. Carbohydrate binding modules are classified into families and CBMs classed as members of the family 40 CBMs (CBM40) may be useful. The family 40 CBMs embrace molecules of approximately 200 residues and are often found at the N-terminus of GH33 sialidases. They may also be found inserted in the β-propeller of GH33 sialidases.

Exemplary carbohydrate binding modules for use may comprise the sialic acid binding domain of *Vibrio cholerae* NanH sialidase (VcCBM: a CBM40) and/or the equivalent (or homologous) domain from *Streptococcus pneumoniae* NanA sialidase (SpCBM: also a CBM40). Of course similar or homologous sialic acid binding modules present in other organisms are to be encompassed within the scope of the term "CBM".

An exemplary *Vibrio cholerae* NanH sialidase amino acid sequence is deposited under accession umber A5F7A4 and is reproduced below as SEQ ID NO: 1 (781 amino acids).

```
MRFKNVKKTA LMLAMFGMAT SSNAALFDYN ATGDTEFDSP AKQGWMQDNT NNGSGVLTNA

DGMPAWLVQG IGGRAQWTYS LSTNQHAQAS SFGWRMTTEM KVLSGGMITN YYANGTQRVL

PIISLDSSGN LVVEFEGQTG RTVLATGTAA TEYHKFELVF LPGSNPSASF YFDGKLIRDN

IQPTASKQNM IVWGNGSSNT DGVAAYRDIK FEIQGDVIFR GPDRIPSIVA SSVTPGVVTA

FAEKRVGGGD PGALSNTNDI ITRTSRDGGI TWDTELNLTE QINVSDEFDF SDPRPIYDPS
```

```
SNTVLVSYAR WPTDAAQNGD RIKPWMPNGI FYSVYDVASG NWQAPIDVTD QVKERSFQIA

GWGGSELYRR NTSLNSQQDW QSNAKIRIVD GAANQIQVAD GSRKYVVTLS IDESGGLVAN

LNGVSAPIIL QSEHAKVHSF HDYELQYSAL NHTTTLFVDG QQITTWAGEV SQENNIQFGN

ADAQIDGRLH VQKIVLTQQG HNLVEFDAFY LAQQTPEVEK DLEKLGWTKI KTGNTMSLYG

NASVNPGPGH GITLTRQQNI SGSQNGRLIY PAIVLDRFFL NVMSIYSDDG GSNWQTGSTL

PIPFRWKSSS ILETLEPSEA DMVELQNGDL LLTARLDFNQ IVNGVNYSPR QQFLSKDGGI

TWSLLEANNA NVFSNISTGT VDASITRFEQ SDGSHFLLFT NPQGNPAGTN GRQNLGLWFS

FDEGVTWKGP IQLVNGASAY SDIYQLDSEN AIVIVETDNS NMRILRMPIT LLKQKLTLSQ

N
```

The CBM region of SEQ ID NO: 1 is from amino acid residue 25 to 216—this sequence may be SEQ ID NO: 2.

An exemplary *Streptococcus pneumoniae* NanA sialidase amino acid sequence has been deposited under accession number P62575 and is reproduced below as SEQ ID NO: 3 (1035 amino acids).

```
MSYFRNRDID IERNSMNRSV QERKCRYSIR KLSVGAVSMI VGAVVFGTSP VLAQEGASEQ

PLANETQLSG ESSTLTDTEK SQPSSETELS GNKQEQERKD KQEEKIPRDY YARDLENVET

VIEKEDVETN ASNGQRVDLS SELDKLKKLE NATVHMEFKP DAKAPAFYNL FSVSSATKKD

EYFTMAVYNN TATLEGRGSD GKQFYNNYND APLKVKPGQW NSVTFTVEKP TAELPKGRVR

LYVNGVLSRT SLRSGNFIKD MPDVTHVQIG ATKPANNTVW GSNLQIRNLT VYNRALTREE

VQKRSQLFKR SDLEKKLPEG AALTEKTDIF ESGRKGKPNK DGIKSYRIPA LLKTDKGTLI

AGADERRLHS SDWGDIGMVI RRSEDNGKTW GDRVTITNLR DNPKASDPSI GSPVNIDMVL

VQDPETKRIF SIYDMFPEGK GIFGMSSQKE EAYKKIDGKT YQILYREGEK GAYTIRENGT

VYTPDGKATD YRVVVDPVKP AYSDKGDLYK GNQLLGNIYF TTNKTSPFRI AKDSYLWMSY

SDDDGKTWSA PQDITPMVKA DWMKFLGVGP GTGIVLRNGP HKGRILIPVY TTNNVSHLNG

SQSSRIIYSD DHGKTWHAGE AVNDNRQVDG QKIHSSTMNN RRAQNTESTV VQLNNGDVKL

FMRGLTGDLQ VATSKDGGVT WEKDIKRYPQ VKDVYVQMSA IHTMHEGKEY IILSNAGGPK

RENGMVHLAR VEENGELTWL KHNPIQKGEF AYNSLQELGN GEYGILYEHT EKGQNAYTLS

FRKFNWDFLS KDLISPTEAK VKRTREMGKG VIGLEFDSEV LVNKAPTLQL ANGKTARFMT

QYDTKTLLFT VDSEDMGQKV TGLAEGAIES MHNLPVSVAG TKLSNGMNGS EAAVHEVPEY

TGPLGTSGEE PAPTVEKPEY TGPLGTSGEE PAPTVEKPEY TGPLGTAGEE AAPTVEKPEF

TGGVNGTEPA VHEIAEYKGS DSLVTLTTKE DYTYKAPLAQ QALPETGNKE SDLLASLGLT

AFFLGLFTLG KKREQ
```

The CBM region of SEQ ID NO: 3 is from amino acid residue 121 to 305—this sequence may be SEQ ID NO: 4.

Thus, CBMs for use as sialic acid binding molecules in the various aspects and embodiments of this disclosure may comprise a protein or peptide having the sequence of SEQ ID NO: 1, 2, 3 or 4 or a sequence fragment derived therefrom and which encodes a molecule with an ability to bind sialic acid (in other words a sialic acid binding molecule encoding portion of fragment of SEQ ID NOS: 1, 2, 3 or 4).

A useful sialic acid binding molecule may comprise a proteinaceous moiety encoded by the sialic acid binding domain of the nanH gene (encoding sialidase) of *V. cholerae* (as provided by SEQ ID NO: 1) or an equivalent or homologous gene present in another organism (for example the equivalent/homologous nanA sialidase gene of *S. pneumoniae*: see SEQ ID NO: 3).

A sialic acid binding molecule for use may comprise from about residue 1, 5, 10, 15, 25 or 30 (i.e. from 1-30 or from any amino acid residue there between) to about residue 150, 175, 200, 210, 216, 220-781 (to any residue from 150 to 781 including any residue therebetween) of the *V. cholerae* sialidase molecule of SEQ ID NOS: 1 and 2. For example a sialic acid binding molecule for use may comprise a peptide having a sequence corresponding to residue 25 to about residue 216 of SEQ ID NO: 1 above.

A further suitable sialic acid binding molecule may comprise a protein or peptide having the sequence of SEQ ID NO: 3 or 4 or a sialic acid binding fragment thereof. For example, a useful sialic acid binding molecule may comprise a proteinaceous moiety encoded by the sialic acid binding domain of the *Streptococcus pneumoniae* nanA gene (encoding sialidase). For example a sialic acid binding molecule for use may comprise from about residue 80, 90, 100, 110, 120, 121 to 130 (i.e. from any of about residues 80 to 130 including any residue therebetween) to about residue 250, 275, 300, 305, 310, 320-1035 (i.e. to any residue from about 250-1035 including to about any residue therebetween) of the *S. pneumoniae* sialidase molecule of SEQ ID NOS: 3 and 4. For example, a sialic acid binding molecule for use may comprise a peptide having a sequence corresponding to residue 121 to about residue 305 of SEQ ID NO: 3 above.

A sialic acid binding molecule for use may comprise one or more CBMs. For example, suitable sialic acid binding molecules may comprise single CBMs—for example a single VcCBM or a single SpCBM. Alternatively, a sialic acid binding molecule for use may comprise a plurality or multiple (i.e. two or more) CBMs. Sialic acid binding molecules which comprise a plurality of CBMs may be termed "multivalent sialic acid binding molecules" or "multivalent CBMs". A multivalent CBM may, for example, comprise two or more (for example three, four, five or six) VcCBMs or two or more SpCBMs. A multivalent CBM may comprise a mixture of different CBMs, for example one or more VcCBMs with one or more SpCBMs.

Thus, the various aspects and embodiments of this disclosure (uses, sialic acid binding molecules for use, methods and medicaments) may exploit sialic acid binding molecules which comprise, consist of or consist essentially of sialic acid binding molecules selected from the group consisting of:
(i) one or more VcCBM(s);
(ii) one or more SpCBM(s); and
(iii) a multivalent CBM.

As such, the present disclosure provides Vc4CBM for use in the treatment and/or prevention of sepsis and/or one or more symptoms thereof.

Further provided is the use of Vc4CBM in the manufacture of a medicament for use in the treatment and/or prevention of sepsis and/or one or more symptoms thereof.

The disclosure also relates to a method of treating or preventing sepsis and/or one or more symptoms thereof, said method comprising the steps of administering to a subject in need thereof, a therapeutically effective amount of Vc4CBM.

For the avoidance of doubt, Vc4CBM comprises, consists essentially of or consists of four *Vibrio cholerae* NanH sialidase CBM units linked, bound or conjugated together. Vc4CBM may be described as a tandem-repeat multivalent protein based on the Family 40 sialic acid binding domain (CBM) of the nanH gene encoding the sialidase from *V. cholerae*. Molecules of this type may be generated using PCR-based cloning techniques and a suitable method for the generation of multivalent molecules of this type is described in, for example, Connaris et al, 2009 (Enhancing the Receptor Affinity of the Sialic Acid-Binding Domain of *Vibrio cholerae* Sialidase through multivalency; J. Biol. Chem; Vol. 284(11); pp 7339-7351). For example, multivalent CBM molecules, including the likes of Vc4CBM may be prepared as constructs comprising multiple CBMs linked by amino acid/peptide linkers. Each CBM (for example VcCBM) may be linked to another by, for example, peptides comprising 5, 10 or 15 amino acids. By way of example any one or more of the following peptides may be used to link two or more CBMs to produce a multivalent CBM:

```
(1) 5 amino acid linkers:
ALNGS
LQALG
GGNSG (ii) 10 amino acid linkers:
ALNGSGGGSG
LQALGGGGSL (iii) 15 amino acid linkers:
ALNGSGGGSGGGGSG
```

Figure 8:
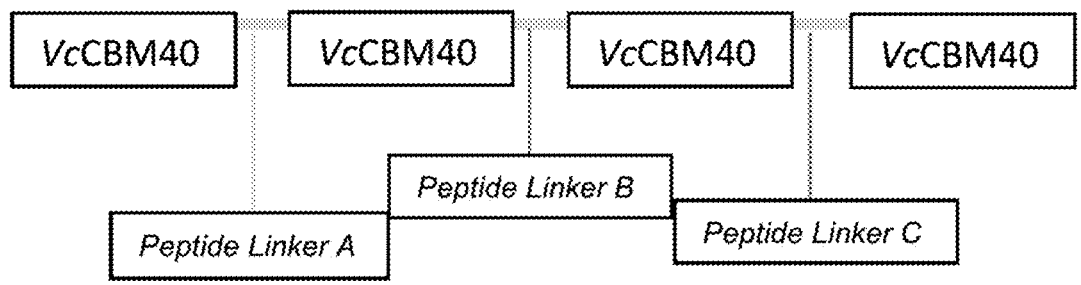

As shown in FIG. 8, a Vc4CBM molecule may conform to General Formula 1, wherein Peptide Linkers A, B and/or C are selected from the linker options presented above as (i), (ii) and/or (iii). It should be noted that the term "VcCBM40" embraces not only the complete family 40 CBM derived from *Vibrio cholerae* (NanH sialidase) but also sialic acid binding fragments derived therefrom. Indeed, each of the VcCBM units shown in General Formula 1 may be selected from the group consisting of:

(i) a *Vibrio cholerae* NanH sialidase CBM; and (ii) a *Vibrio cholerae* NanH sialidase CBM sialic acid binding fragment thereof.

Thus, each of the VcCBM units of the molecule shown in General Formula 1 may be the same or different.

The sialic acid binding molecules for use may further comprise an oligomerisation domain. Suitable oligomerisation domains may exhibit an ability to self-associate to form multimer structures, for example trimers. An oligomerisation domain for use may comprise any molecule with the above mentioned oligomerisation properties or any functional fragment thereof. For example, one or more (for example two) sialic acid binding molecules (for example CBMs) may be bound, coupled or fused to an oligomerisation domain—the resulting sialic acid binding molecule:: oligomerisation domain "fusion" may then be used (with one or more other such "fusions") as a molecule for modulating cell growth and/or activity and/or for treating or preventing any of the diseases and/or conditions disclosed herein.

Suitable oligomerisation domains may be derived from, for example, *Pseudomonas aeruginosa* pseudaminidase. An exemplary *Pseudomonas aeruginosa* pseudaminidase sequence amino acid sequence has been deposited under accession number PAO579 and is reproduced below as SEQ ID NO: 5 (438 amino acids).

```
MNTYFDIPHR LVGKALYESY YDHFGQMDIL SDGSLYLIYR RATEHVGGSD GRVVESKLEG

GIWSAPTIVA QAGGQDFRDV AGGTMPSGRI VAASTVYETG EVKVYVSDDS GVTWVHKFTL

ARGGADYNFA HGKSFQVGAR YVIPLYAATG VNYELKWLES SDGGETWGEG STIYSGNTPY

NETSYLPVGD GVILAVARVG SGAGGALRQF ISLDDGGTWT DQGNVTAQNG DSTDILVAPS

LSYIYSEGGT PHVVLLYTNR TTHFCYYRTI LLAKAVAGSS GWTERVPVYS APAASGYTSQ
```

```
-continued
VVLGGRRILG NLFRETSSTT SGAYQFEVYL GGVPDFESDW FSVSSNSLYT LSHGLQRSPR

RVVVEFARSS SPSTWNIVMP SYFNDGGHKG SGAQVEVGSL NIRLGTGAAV WGTGYFGGID

NSATTRFATG YYRVRAWI
```

The oligomerisation domain of SEQ ID NO: 5 is from amino acid residue 333 to 438—this sequence may be SEQ ID NO: 6.

Thus an oligomerisation domain for use may comprise from about residue 250, 275, 300, 310, 320, 333, 340 to 350 (i.e. from about residue 250 to about residue 350 including from about any residue therebetween) to about residue 400, 410, 420, 430 or 438 (i.e. to about any residue from about residue 400 residue 438 including to about any residue therebetween) of the *P. aeruginosa* pseudaminidase trimerisation domain (PaTD) provided by SEQ ID NO: 5. For example, a useful sialic acid binding molecule may exploit an oligomerisation domain comprising residues 333 to 438 of SEQ ID NO: 6.

A sialic acid binding molecule for use may comprise one or more of the CBM based molecules presented in FIG. 1. For example, a suitable sialic acid binding molecule may comprise (consist essentially of, or consist of) two or more VcCBMs optionally fused, bound or conjugated to an oligomerisation domain (such as a PaTD or oligomerisation fragment thereof). The sialic acid binding molecule may comprise, consist or consist essentially of two fused (or bound) VcCBMs which are in turn fused to an oligomerisation domain (see, for example, molecule Vc2CBMTD shown in FIG. 1).

Other sialic acid binding domains for use may comprise two or more SpCBMs optionally fused, bound or conjugated to an oligomerisation domain (such as a PaTD or an oligomerisation fragment thereof). Sialic acid binding molecules for use may comprise, consist or consist essentially of two fused (or bound) SpCBMs which are in turn fused to an oligomerisation domain (see, for example, molecule Sp2CBMTD shown in FIG. 1).

Given that sepsis is characterised by an exacerbated host immune response, the sialic acid binding molecules of this disclosure (including, for example, Vc4CBM) may find application in compositions, medicaments and methods for modulating sepsis associated immune responses. A sepsis associated immune response may be an immune response that, when compared to a normal immune response (e.g. one that is not a sepsis associated immune response) is exacerbated, exaggerated and/or inappropriate. As stated, the sepsis associate immune response may lead to host tissue damage and/or organ damage/failure and may comprise the dysregulation of innate immune responses as well as the production and/or over/under production of certain cytokines and/or pro-coagulation cytokines (including, for example, tumor necrosis factor, interleukin 1 and interleukin 6). Again, any dysregulation and/or cytokine over/under production may be measured, quantified and/or determined relative to the level of cytokine under/over-production and/or regulation in an uninfected host.

Thus, the disclosure provides a sialic acid binding molecule for use in modulating (for example dampening, inhibiting and/or ablating) a sepsis associated immune response. The disclosure may further relate to a method of modulating a sepsis associated immune response, said method comprising administering a subject in need thereof (the subject being a subject (i) suffering from sepsis and/or with a sepsis associated immune response or (ii) predisposed or susceptible thereto). The disclosure also provides the use of a sialic acid binding molecule in the manufacture of a medicament for modulating a sepsis associated immune response.

It should be noted that the various uses and methods described herein may comprise the administration of a non-cell cross-linking, non-cell or red/white cell agglutinating, non-blood clotting cascade/symptom and/or non-stroke/thrombosis symptom inducing or activating amount of a sialic acid binding molecule.

Sialic acid binding molecule based treatments, compositions, methods and medicaments (all of which are described herein—in particular those based on Vc4CBM) represent an advantage over prior art equivalents as the sialic acid binding molecules may not induce, cause or accelerate the release of microbial pro-inflammatory components which can exacerbate or induce sepsis and lead to severe sepsis and shock. Further, in contrast to antimicrobial peptides (AMPs), the sialic acid binding molecules are less toxic and less likely to be rendered useless through the development of resistance.

Further, it should be noted that the various uses, methods and medicaments described herein may exploit one or more of the sialic acid binding molecules described herein. For example, two or more different sialic acid binding molecules may be administered to a subject together, concurrently or separately.

The present disclosure may provide compositions for use in the various uses, medicaments and methods described herein. As such, any of the sialic acid binding molecule(s) described herein may be formulated for use. For example, a sialic acid binding molecule (or molecules) may be formulated as therapeutic or pharmaceutical compositions. The various compositions may comprise one or more of the sialic acid binding molecules described herein and any given treatment may require the administration (together, concurrently or separately) of one or more of these compositions.

The various sialic acid binding molecules described herein may be formulated for enteral (including oral), parenteral and/or topical administration and one of skill will appreciate that the precise formulation may vary depending on the route of administration. Pharmaceutical compositions according to the present invention may be prepared conventionally, comprising substances that are customarily used in pharmaceuticals and as described in, for example, Remington's The Sciences and Practice of Pharmacy, 22nd Edition (Pharmaceutical Press 2012) and/or Handbook of Pharmaceutical Excipients, 7th edition (compiled by Rowe et al, Pharmaceutical Press, 2012)—the entire content of all of these documents and references being incorporated by reference.

A therapeutic or pharmaceutical composition of this disclosure (that is a composition comprising a sialic acid binding molecule and for use in any of the medicaments or methods described herein—including the methods of or medicaments for, treating or preventing sepsis) may be formulated together with one or more pharmaceutically acceptable excipients, carriers, adjuvants and buffers. The compositions can be administered, e.g. orally (including mucosally), parentally, enterally, intramuscularly, subcutaneously, intravenously or via any other routes useful to achieve the desired effect (in this case effects which include, modulation of cell growth/activity, treatment or prevention of diseases/conditions associated with the same and/or cancer and/or modulation of tumour growth). As stated, depending on the chosen route of administration, the exact composition of the formulation may vary.

A therapeutic or pharmaceutical formulation comprising a sialic acid binding molecule and for administration to a subject may be coated, encapsulated or enveloped in a material which protects the sialic acid binding molecule from the action of enzymes, acids and other natural compounds/conditions (including, for example, compounds (including antibodies), cells and processes of the immune system) which may inactivate or denature the compound and/or its sialic acid binding properties.

Among the various standard and conventional excipients that may be available for use in compositions comprising sialic acid binding molecules, are those pharmaceutically acceptable organic or inorganic carrier substances which are suitable for parenteral, enteral, oral (including mucosal) and other routes of administration that do not deleteriously react with the sialic acid binding molecule(s).

Where the sialic acid binding molecules are to be formulated for parental administration, the compositions may be sterile.

The composition may comprise an oil-based or aqueous solution, a suspension and/or an emulsion.

In other embodiments, the composition may take the form of an implant, such as for example a (dissolvable or biodegradable) film, pessary or implant (including suppositories).

The pharmaceutical preparations comprising sialic acid binding molecules may be mixed with stabilizers, wetting agents, emulsifiers, salts (for use in influencing osmotic pressure), buffers and/or other substances that do not react deleteriously with the active compounds.

One or more of the sialic acid binding molecules described herein may be formulated for and administered, orally. As stated, oral administration would include mucosal administration which would itself would include administration intranasally and/or by inhalation.

Compositions for use may include solid dosage forms which are suitable for oral administration. These may include, for example, capsules, tablets, pills, powders, and granules. In any given solid dosage form, the sialic acid binding molecule may be admixed with at least one inert pharmaceutically-acceptable excipient. Examples of suitable excipients will be known to one of skill in this field but may include, for example, fillers or extenders, humectants, wetting agents, binders, disintegrating agents, solution retarders, absorption accelerators, adsorbents, lubricants or mixtures thereof. A tablet, pill or capsule may further comprise a buffering agent. Solid dosage forms such as tablets, dragees, capsules, pills and/or granules also can be prepared with coatings and shells, such as coatings which protect against the gastrointestinal environment and/or stomach acid.

A solid dosage form may contain opacifying agents, and can also be formulated so as to ensure the delayed release of the active agent (in this case the sialic acid binding molecule) in or to a specific part of the intestinal tract.

Solid compositions for oral administration can be formulated in a unit dosage form, each dosage containing an appropriate dose of the sialic acid binding molecule. The exact amount of sialic acid binding molecule contained within any given solid dosage form will vary depending on the intended use. A solid composition may contain a "unit dose"—a unit dose containing a quantity of sialic acid binding molecule calculated to produce the desired effect (for example modulation of cell growth and/or activity) over the course of a treatment period. Liquid dosage forms for oral administration may (as stated) include emulsions, solutions, suspensions, syrups, and elixirs. In addition to the compound or composition, the liquid dosage forms may contain inert diluents commonly used in the art, such as water or other solvents, solubilizing agents and emulsifiers.

Any suitable amount of a sialic acid binding molecule (for example any of the CBM type molecules described herein) may be used. For example, whether a composition comprising a sialic acid binding molecule (for example a CBM such as Vc4CBM or Vc2CBMTD) is to be administered intravenously or mucosally (for example intranasally) the dose of sialic acid binding molecule may comprise anywhere between about 1 μg and about 1000 μg. For example a dose of about (for example +/−0.5 μg) 10 μg, 11 μg, 12 μg, 13 μg, 14 μg, 15 μg, 20 μg, 30 μg, 40 μg, 50 μg, 100 μg, 200 μg, 300 μg, 400 μg, 500 μg, 600 μg, 700 μg, 800 μg, 900 μg or 950 μg of the sialic acid binding molecule may be used. These amounts may be provided in any suitable volume of excipient, diluent or buffer. For example the amount of sialic acid binding molecule may be provided in anywhere between about 1 μl to about 5 ml of excipient, diluent or buffer. For example, the required amount of sialic acid binding molecule may be combined (or formulated) with about 5 μl, 10 μl, 15 μl, 20 μl, 25 μl, 30 μl, 35 μl, 40 μl, 45 μl, 50 μl, 55 μl, 60 μl, 65 μl, 70 μl, 75 μl, 80 μl, 85 μl, 90 μl, 95 μl, 100 μl, 200 μl, 300 μl, 400 μl, 500 μl, 600 μl, 700 μl, 800 μl, 900 μl, 1 ml, 2 ml, 3 ml or 4 ml. For example, for intranasal administration and amount of sialic acid binding molecule (for example about 100 μg or 500 μg) may be formulated in about 50 μl excipient for use as a single dose. Further and for intravenous use, small amounts of sialic acid binding molecule may be used. For example amounts of about 10 μg, 11 μg or 12.5 μg, 13 μg, 14 μg or 15 μg may be used intravenously.

DETAILED DESCRIPTION

The present invention will now be described in detail with reference to the following figures which show:

FIG. 1: Building blocks of the multivalent CBM forms and their affinities for sialic acid. a, VcCBM, residues 25-216 of the *V. cholerae* sialidase (PDB:1w0p) with α-2,3-sialyllactose drawn as spheres. b, SpCBM, residues 121-305 of *S. pneumoniae* NanA sialidase with α-2,3-sialyllactose (PDB:4c1w). c, TD, the trimerisation domain, residues 333-438, of the *P. aeruginosa* pseudaminidase (PDB:2w38) in rainbow colours; the other two monomers in single colors. d, Multivalent forms: their molecular weights, valencies and binding affinities for α2,3-sialyllactose as determined by surface plasmon resonance (SPR) at 25° C. ($K_D$ values for VcCBM, Vc2CBM and Vc3CBM had been reported previously[7]). Tandem repeat CBMs, and oligomeric CBMs fused to TD are linked by a 5-amino linker (details in Full Methods).

FIG. 2: Survival time of mice infected intravenously only with $8.5\times10^5$ CFU/mouse (control) or with same number of pneumococci plus 12.5 μg/mouse Vc4CBM. The protein was administered with bacterial inoculums and mice were observed for 168 h. The survival time of each animal is shown with a dot. The median survival time is given with a horizontal line and was 59 h (SD: 53) for control and 84 h (SD:55) for Vc4CBM group.

FIG. 3: Survival time of mice infected intravenously only with approximately $6.3\text{-}7.5\times10^5$ CFU/mouse (control) or with same number of pneumococci plus 13-15 µg/mouse Vc4CBM. The protein was administered with bacterial inoculums and mice were observed for 168 h. The survival time of each animal is shown with a dot. The median survival time is given with a horizontal line and was 59 h (SD: 48.7) for control and 168 h (SD:48.5) for Vc4CBM-treated group.

Figure 4:
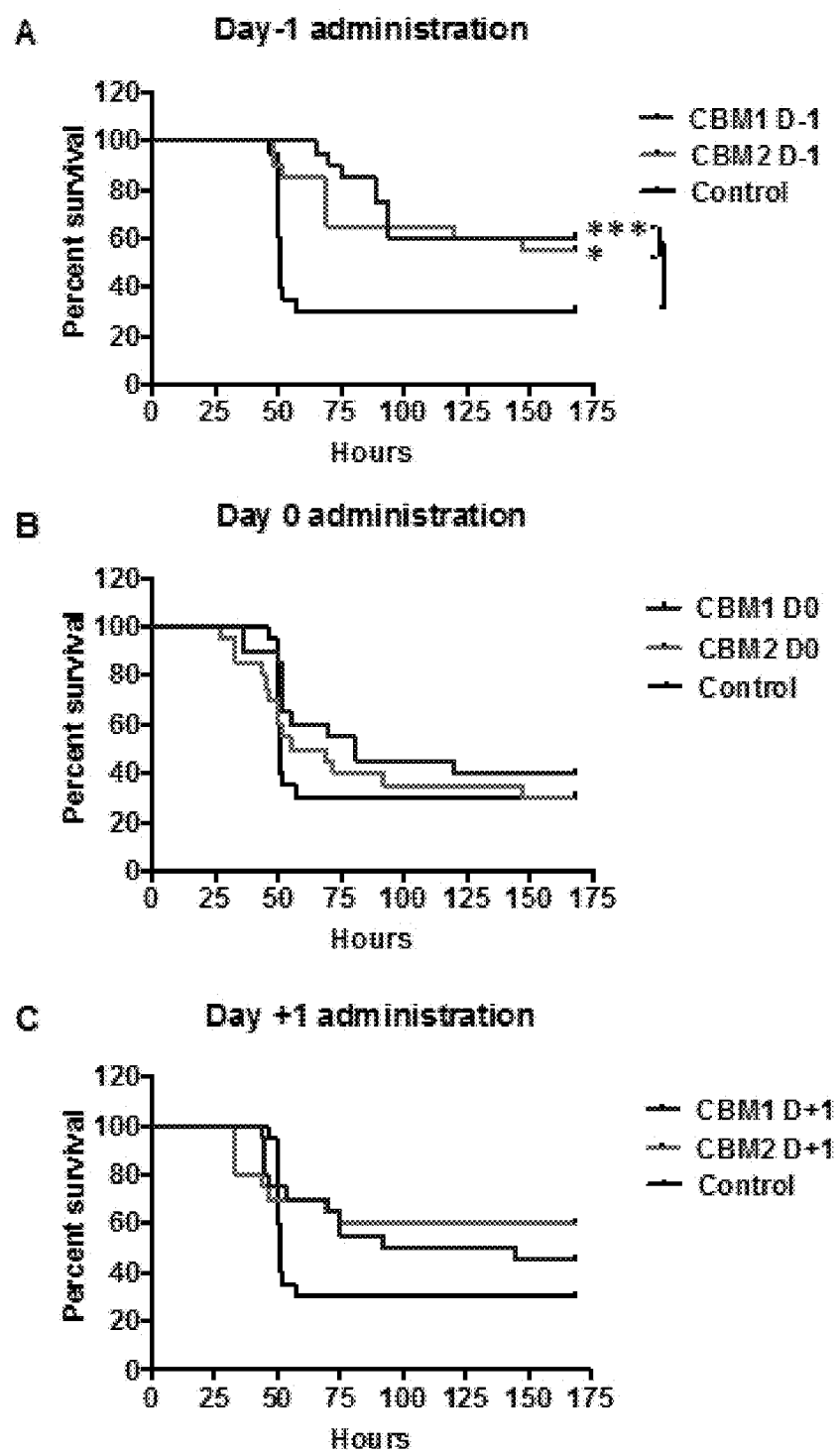

FIG. 4: The effect of intranasal administration of two mCBM40s on survival of Streptococcus pneumoniae D39-infected mice. CD1 outbred mice (n=20) were administered intranasally with either a single dose of 500 µg Vc4CBM (CBM1) or 100 µg Vc2CBMTD (CBM2) a day before (A), at the time of (B) or 1 day after intranasal infection (C) with S. pneumoniae D39. Control group received PBS only. Difference in percent median survival was calculated using Wilcoxon test. *$p<0.05$, ***$p<0.001$ relative to the control that received PBS.

Figure 5:
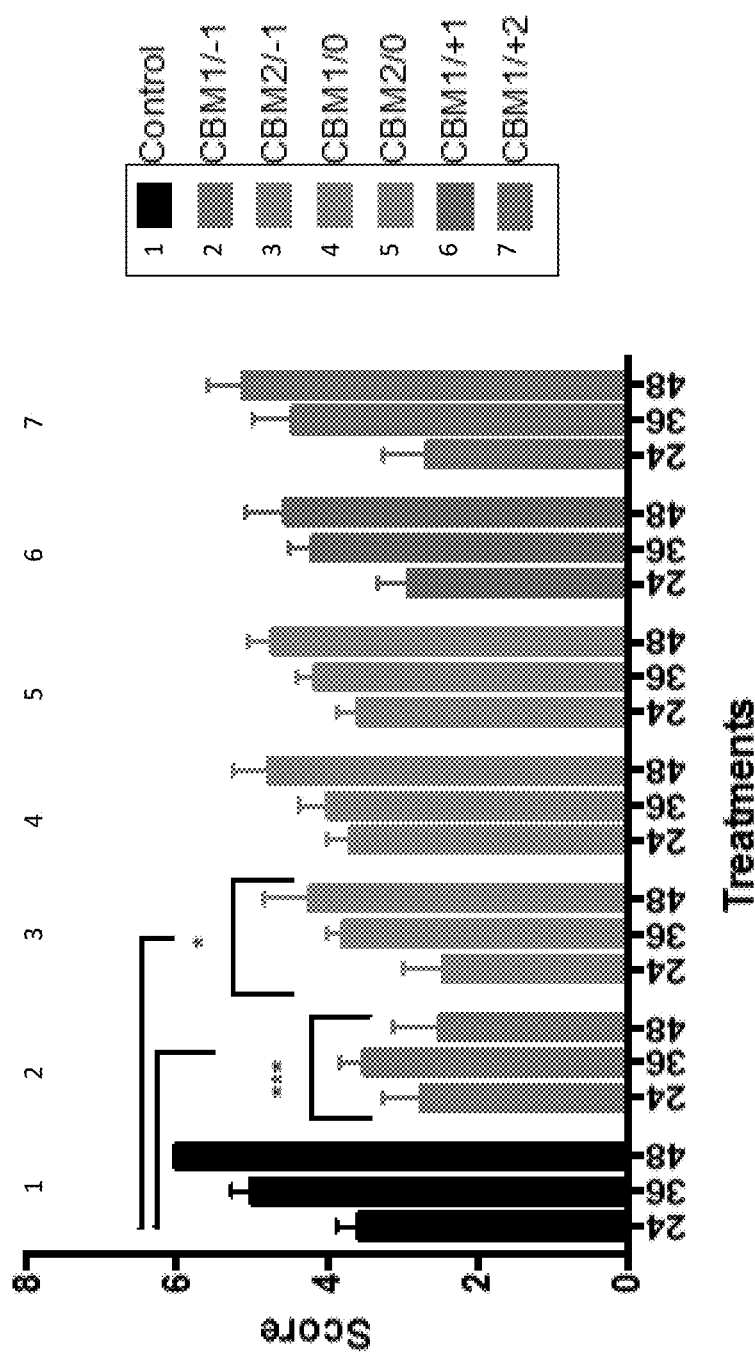
Figure 6:
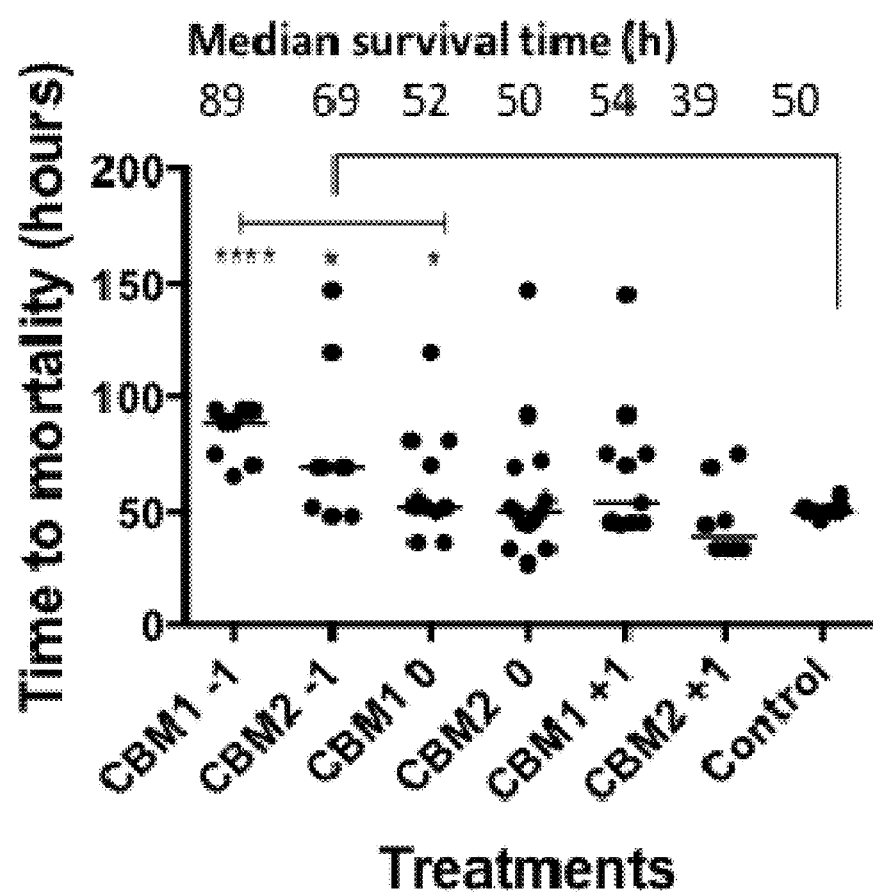

FIG. 5: The impact of mCBM40s on disease sign scores in pneumococcal infection. CD1 mice that received either 500 µg Vc4CBM (CBM1) or 100 µg Vc2CBMTD (CBM2) a day before (−1), at the time of (0) or 1 day after (+1) intranasal infection when administered with a lethal dose of S. pneumoniae D39, were monitored for signs of disease at 24, 36 and 48 h post infection. A score of 2, 4, or 6 was given if the animals were piloerect, hunched, or lethargic, respectively. Each column represents the mean disease sign scores at different time points for 8 to 14 animals that eventually died. The vertical lines are for standard error of mean. Data was analysed by two-way ANOVA followed by Dunnett's multiple comparisons test. *$p<0.05$, ***$p<0.001$ FIG. 6: The effect of mCBM40s on mortality time of Streptococcus pneumoniae infected mice after intranasal administration. CD1 mice were administered intranasally with either 500 Vc4CBM (CBM1) or 100 µg Vc2CBMTD (CBM2) a day before (−1), at the time of (0) or 1 day after intranasal infection (+1) with S. pneumoniae D39. Difference in time to mortality was calculated using Mann-Whitney U test. *$p<0.05$, ****$p<0.0001$ relative to the control that received PBS.

Figure 7:
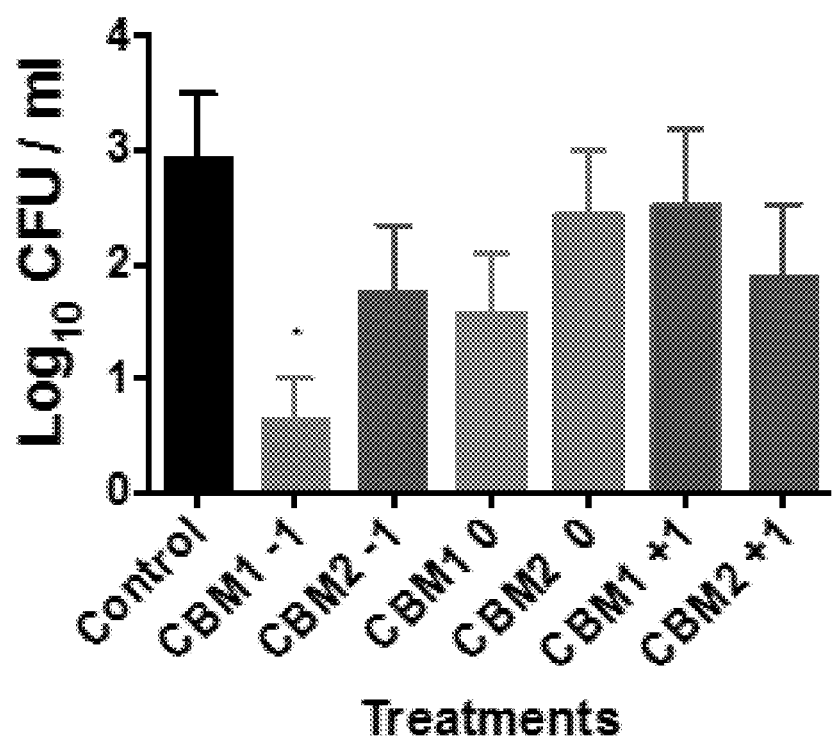

FIG. 7: The impact of CBM protein on pneumococcal bacteremia: CD1 mice received either 500 µg Vc4CBM (CBM1) or 100 µg Vc2CBMTD (CBM2) a day before (−1), at the time of (0) or 1 day after (+1) intranasal infection with lethal dose of S. pneumoniae D39. A blood sample was taken from the tail vein 24 h post infection and CFU/ml was determined by serial dilution and plating. Each column represents the mean CFU/ml for 8 to 14 animals. Vertical lines are for standard error of mean. Data was analysed by two-way ANOVA followed by Dunnett's multiple comparisons test. *$p<0.05$ relative.

FIG. 8: A schematic referred to hereinafter as General Formula 1. An exemplary Vc4CBM may take the form of General Formula 1.

EXAMPLE 1

When identifying different routes of mCBM40 delivery in vivo, it was noted that a tetrameric Vc-based CBM40 (Vc4CBM), protected mice when given intravenously with a lethal dose of Streptococcus pneumoniae. This suggests a role for CBMs (including multivalent molecules comprising the same) in the treatment and/or prevention of sepsis, its symptoms and/or associated pathologies.

Multivalent forms of CBM40s target sialylated cell surfaces and therefore it was expected that, at certain concentrations, agglutination of red (and white) blood cells in vivo would occur as a result of cross-linking protein-ligand interactions between cells. This could potentially lead to a number of blood clotting symptoms such as thrombosis or stroke.

The results of initial dose-response intravenous Vc4CBM dosing in mice and clinical activity show that an intravenous Vc4CBM dose of 12.5 µg/mouse was tolerated.

Production of the Vc4CBM in E. coli meant that it was necessary to eliminate contamination of the CBM preparation with endotoxin as the cause of any observed adverse events—this would ensure that the results represented a proper assessment of the effect the Vc4CBM molecule against sepsis. As stated an intravenous dose of 12.5 µg Vc4CBM was tolerated by mice and a pneumococcal challenge was attempted.

Figure 2:
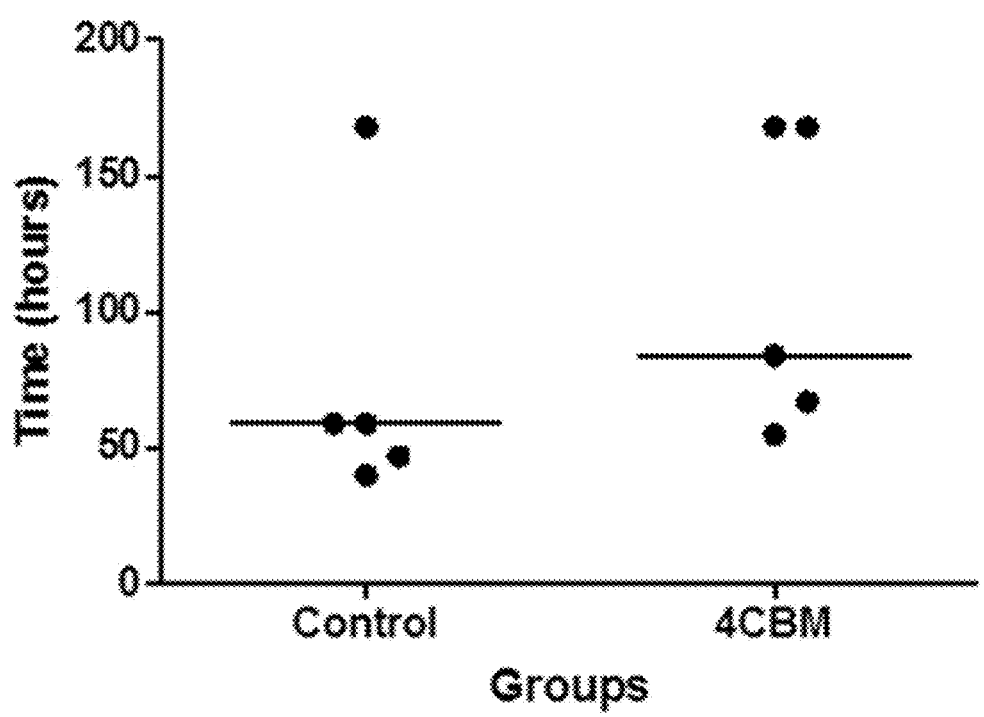
Figure 3:
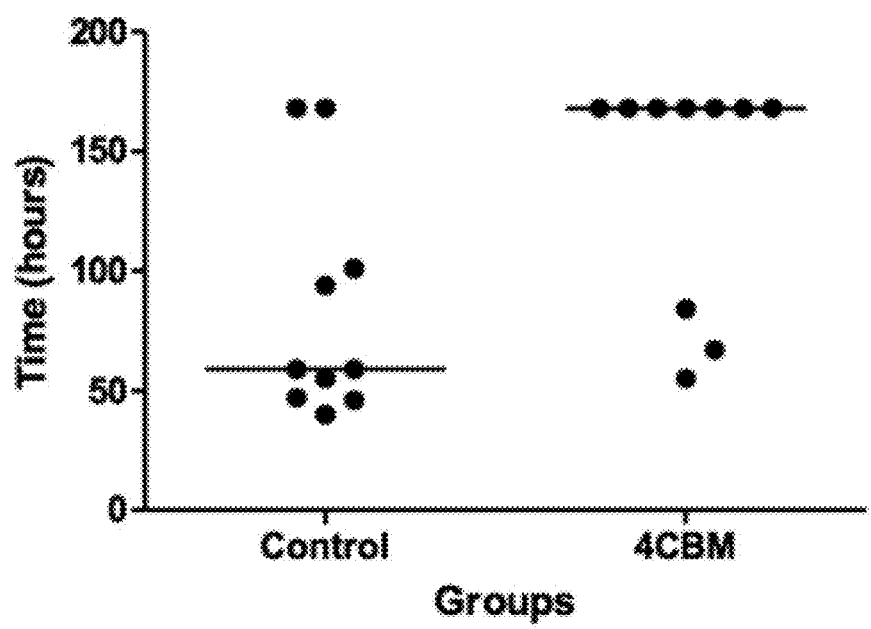

Groups of mice (n=5) were infected intravenously with a lethal dose of pneumococcus ($8.5\times10^5$ CFU/mouse) in the presence or absence of a single dose of Vc4CBM (12.5 µg/mouse). Survival times of mice are shown in FIG. 2. There appeared to be a slight, increase in survival of mice in the CBM-treated group (median survival time ~84 h) compared to the control group (59 h). To determine whether the survival rate in mice could be improved, a further study was performed whereby the pneumococcal CFU dose was slightly reduced to correspond with a slight increase in the amount of Vc4CBM given intravenously. The results of this experiment are shown in FIG. 3. Here it appears that the survival rate of mice improved significantly under the conditions tested, with a combined survival rate of 70% after 7 days in the CBM-treated groups, displaying a median survival time of 168 h, compared to 20% survival of mice in the untreated, infected groups (median survival time of 59 h).

These results indicate that mCBM40s have the potential to alleviate symptoms of sepsis in a bacterially-infected host. In the case of Vc4CBM, it is likely that this biologic modulates the immune response by dampening down the pro-inflammatory cascade of a S. pneumoniae infection that leads to sepsis. Further, while there was a concern that the multivalent CBMs might (through the cross-linking of protein-ligand interactions between cells) induce agglutination of cells (including red (and white) blood cells) in vivo (which could potentially lead to the induction of blood clotting cascades and a number of blood clotting symptoms such as thrombosis or stroke), this did not occur.

EXAMPLE 2

Novel, bacterially-derived, proteins (mCBM40s) that target and bind host cell surface sialic acid-receptors with high affinity (JBC (2009), 284, 7339) have been engineered. When mCBM40s are administered in mice, they are shown to be non-toxic and can protect mice from respiratory pathogens (PNAS (2014) 111, 6401; AAC 59(3): 1495-1504). Using a pneumococcal-challenged mouse model, it has been shown that mCBM40, Vc4CBM can provide significant survival rates in mice against a lethal pneumococcal infection. To further evaluate the protective utility of mCBM40 proteins in reducing bacteraemia in a pneumococcal mouse model, mCBM40s were also given intranasally (as described below).

mCBM40 Dosing Via the Intranasal Route

Method: All CBM40 proteins (Vc4CBM and Vc2CBMTD, endotoxin-free) were prepared as described in Connaris et al (2014)[10]. Groups of female mice (CD1 outbred strain, n=10 to 20), weighing 28-35 g, were intranasally administered with a single dose of either Vc4CBM (up to 500 µg) or Vc2CBMTD (up to 100 µg) in 50 µl sterile PBS, either one day before (D−1), on the day (D0) or one day after (D+1) a lethal intranasal challenge with approximately 1×10⁶ CFU of S. pneumoniae D39 (in 50 μl of PBS)/mouse. The control group received PBS only. Clinical signs of disease were monitored and recorded over 7 days (168 h), where an ascending score from 0 to 6 (0 being no clinical symptoms) was given to all animals. At the end of experiment, the lungs, and blood will be collected and bacterial counts determined. Bacteraemia was monitored by sampling blood at specific time-points during infection, with the number of colony forming units from blood determined using the technique as described by Miles and Misra[11].

TABLE 1

The impact of mCBM40 dosing on survival of CD1 mice challenged with a lethal pneumococcal dose.
*Survival of treated groups was evaluated after 168 h.

| Treatments | Dead | Survived | % Survival* |
|---|---|---|---|
| CBM1/−1 | 8 | 12 | 60 |
| CBM1/0 | 12 | 8 | 40 |
| CBM1/+1 | 11 | 9 | 45 |
| CBM2/−1 | 9 | 11 | 55 |
| CBM2/0 | 14 | 6 | 30 |
| CBM2/+1 | 8 | 12 | 60 |
| Control (PBS) | 14 | 6 | 30 |

SUMMARY 1. mCBM40s demonstrated reduction of bacteraemia in mice when intranasally given in a lethal pneumococcal infection model.

REFERENCES

1. "The Third International Consensus Definitions for Sepsis and Septic Shock (Sepsis-3)". Feb. 23, 2016. doi:10.1001/jama.2016.0287.
2. Jawad, I; Lukšić, I; Rafnsson, S B (2012). Assessing available information on the burden of sepsis: Global estimates of incidence, prevalence and mortality. Journal of Global Health 2 (1): 010404.
3. Hoffman, S J; Outterson, K; Røttingen, J A; Cars, O; Clift, C; Rizvi, Z; Rotberg, F; Tomson, G; Zorzet, A (2015). An international legal framework to address antimicrobial resistance. Bulletin of the World Health Organization 93 (2): 66.
4. Bahar, A A; Ren, D (2013) Antimicrobial Peptides. Pharmaceutical (Basel) 6 (12): 1543-1575.
5. Yeaman, M R; Yount, N Y (2003) Mechanisms of antimicrobial peptide action and resistance. Pharmacol. Rev. 55:27-55
6. Fox, J L (2013). Antimicrobial peptides stage a comeback. Nature Biotechnology 31: 379-382
7. Connaris, H; Crocker, P R; Taylor, G L (2009). Enhancing the receptor affinity of the sialic acid-binding domain of Vibrio cholerae sialidase through multivalency. J. Biol. Chem. 284(11): 7339-51
8. Connaris, H; Govorkova, E A; Ligertwood, Y; Dutia, B M; Yang, L; Tauber, S; Taylor, M A; Alias, N; Haga, R; Nash, A A; Webster R G; Taylor G L (2014). Prevention of influenza by targeting host-receptors using engineered proteins. PNAS 111(17): 6401-6406.
9. Govorokova, E A; Baranovich, T; Marathe, B M; Yang, L; Taylor, M A; Webster, R G; Taylor, G L; Connaris, H (2015). Sialic acid-binding protein Sp2CBMTD protects mice against lethal challenge with emerging influenza A (H7N9) virus. AAC 59(3): 1495-1504.
10. Connaris H, Govorkova E A, Ligertwood Y, Dutia B M, Yang L, Tauber S, Taylor M A, Alias N, Hagan R, Nash A A, Webster R G, Taylor G L. 2014. Prevention of influenza by targeting host receptors using engineered proteins. *Proc Natl Acad Sci USA* 111:6401-6406.
11. Miles, A A; Misra, S S; Irwin, J O (November 1938). "The estimation of the bactericidal power of the blood.". *The Journal of Hygiene*. 38 (6): 732-49.

The invention claimed is:

1. A method of treating and/or preventing sepsis and/or one or more symptoms thereof, said method comprising administering a sialic acid binding molecule to a subject who has sepsis or an infection which could lead to sepsis or a subject diagnosed as suffering from one or more sepsis associated pathologies, wherein the sialic acid binding molecule comprises two or more family 40 carbohydrate binding molecules.

2. The method of claim 1, wherein the sialic acid binding molecule comprises the sialic acid binding domain of *Vibrio cholerae* NanH sialidase and/or the sialic acid binding domain of *Streptococcus pneumoniae* NanA sialidase.

3. The method claim 2, wherein the *Vibrio cholerae* NanH sialidase comprises the amino acid sequence of SEQ ID NO: 1 or 2.

4. The method of claim 2, wherein the *Streptococcus pneumoniae* NanA sialidase comprises the amino acid sequence of SEQ ID NO: 4.

5. The method of claim 1, wherein the sialic acid binding molecule comprises (i) four *Vibrio cholerae* NanH sialidase CBM units linked, bound, or conjugated together (Vc4CBM); and/or (ii) two *Vibrio cholerae* NanH sialidase CBM units fused, bound, or conjugated to a *Pseudomonas aeruginosa* pseudaminidase trimerisation domain (Vc2CBMTD).

6. The method of claim 1, wherein the sialic acid binding molecule is formulated for oral, mucosal or parenteral administration.

7. The method of claim 1, wherein the sialic acid binding molecule is formulated for intranasal administration.

8. The method of claim 1, wherein the sialic acid binding molecule is formulated for intravenous administration.

* * * * *

UNITED STATES PATENT AND TRADEMARK OFFICE
CERTIFICATE OF CORRECTION

Page 1 of 1

PATENT NO. : 10,953,078 B2
APPLICATION NO. : 16/332920
DATED : March 23, 2021
INVENTOR(S) : Connaris et al.

It is certified that error appears in the above-identified patent and that said Letters Patent is hereby corrected as shown below:

On the Title Page

(30) Foreign Application Priority Data:
Please correct "1616009" to read -- 1616009.5 --

(56) References Cited, FOREIGN PATENT DOCUMENTS, Column 2, Line 4:
Please correct "WO 00/10398" to read -- WO 00/10388 --

(56) References Cited, OTHER PUBLICATIONS, Column 2, Line 19, Baradaran et al. cite:
Please correct "Newcastie" to read -- Newcastle --

(56) References Cited, OTHER PUBLICATIONS, Column 2, Line 31, Connaris et al. cite:
Please correct "6401-6408" to read -- 6401-6406 --

In the Specification

Column 1, Line 48:
Please correct "microbial resistances" to read -- microbial resistance$^5$ --

Column 1, Line 56:
Please correct "models$^{5,9}$" to read -- models$^{8,9}$ --

Column 13, Line 34:
Please correct "500 Vc4CBM" to read -- 500 μg Vc4CBM --

In the Claims

Column 31, Lines 17-18, Claim 1:
Please correct "SEQ ID NO:1 or 2" to read -- SEQ ID NO:2 --

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*